United States Patent [19]

Giencke et al.

[11] Patent Number: 5,258,520
[45] Date of Patent: Nov. 2, 1993

[54] PROCESS FOR PREPARING SUBSTITUTED 2-CYANOPYRIDINES

[75] Inventors: Wolfgang Giencke; Jan Vermehren, both of Hofheim am Taunus, Fed. Rep. of Germany

[73] Assignee: Hoechst Aktiengesellschaft, Frankfurt am Main, Fed. Rep. of Germany

[21] Appl. No.: 3,648

[22] Filed: Jan. 13, 1993

[30] Foreign Application Priority Data

Jan. 15, 1992 [DE] Fed. Rep. of Germany ....... 4200820

[51] Int. Cl.$^5$ .................. C07D 213/57; C07D 213/84
[52] U.S. Cl. .................................................. 546/286
[58] Field of Search ........................................ 546/286

[56] References Cited

U.S. PATENT DOCUMENTS 4,212,980 7/1980 Butler .................................. 546/288

FOREIGN PATENT DOCUMENTS 034349 2/1981 European Pat. Off.
0319254 11/1988 European Pat. Off.

OTHER PUBLICATIONS

Fife, Wilmer K., "Regioselective Cyanation of Pyridine 1-Oxides with Trimethylsilanecarbonitrile", J. Org. Chem. 48: 1357-1377 (1983).
Search Report for EPA 93100148.1.
Fife, Wilmer K., "Regioselective Cyanation of Pyridine 1-Oxides with Trimethylsilanecarbonitrile: A Modified Reissert-Henze Reaction", J. Org. Chem. 48:1375-1377 (1983).
Organic Syntheses, Collective vol. 5, p. 269, (1973).

Primary Examiner—C. Warren Ivy
Assistant Examiner—D. Margaret M. Mach
Attorney, Agent, or Firm—Curtis, Morris & Safford

[57] ABSTRACT

Compounds of the formula I

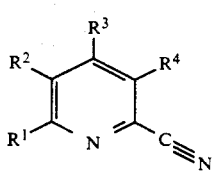

in which $R^1$ is H, alkyl, alkenyl, alkynyl, haloalkyl, alkoxycarbonyl, alkoxyalkyl, phenyl, benzyl or phenoxyalkyl, it being possible for the three latter radicals to be substituted in the phenyl moiety;
$R^2$ is H, alkyl, alkenyl, alkynyl, haloalkyl or alkoxycarbonyl;
$R^3$ is H, alkyl, alkenyl, alkynyl, haloalkyl, alkoxycarbonyl, phenyl, phenoxy, benzyl, it being possible for the three latter radicals to be substituted, or alkoxy; and
$R^4$ is H, alkyl, alkenyl, alkynyl, haloalkyl or alkoxycarbonyl;
or
$R^1$ together with $R^2$ is a saturated chain, and the remaining radicals are as defined above;
or
$R^1$ together with $R^2$ is a chain of the formula —CH=CH—CH=CH—, which may be substituted, and the remaining radicals are as defined above;
or
$R^3$ together with $R^4$ is a chain of the formula —CH=CH—CH=CH—, which may be substituted, and the remaining radicals are as defined above;

are valuable intermediates in the preparation of pharmaceuticals and crop protection agents.

The process according to the invention yields compounds of the formula I by reacting a substituted 1-alkoxypyridinium salt of the formula II,

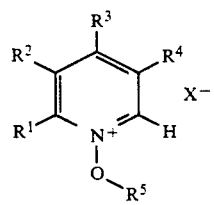

in which
$R^1$ to $R^4$ have the same meaning as in formula I and
$R^5$ is alkyl, alkenyl, alkynyl, benzyl or trialkylsilyl and
X is a leaving group;
together with a cyanide of the formula III $$M(CN)_m \qquad (III)$$

in which
M is alkali metal, alkaline earth metal or copper and m is 1 or 2,
in a polar, aprotic solvent or mixture of solvents.

10 Claims, No Drawings

PROCESS FOR PREPARING SUBSTITUTED 2-CYANOPYRIDINES

DESCRIPTION

The invention relates to a process for preparing substituted 2-cyanopyridines by reacting the corresponding 1-alkoxypyridinium salts with metal cyanides in a polar, aprotic solvent or a mixture of such solvents. Substituted 2-cyanopyridines are valuable intermediates in the preparation of pharmaceuticals and crop protection agents, as have been proposed, for example, in German patent application P 40 32 878.3

Hitherto, substituted 2-cyanopyridines have in the main been prepared by two processes. Either a 1-alkoxypyridinium salt has been reacted with an alkali metal cyanide in water, or pyridine-N-oxides have been reacted with trialkylsilyl cyanides in organic solvents with the aid of an acylating agent such as N,N-dimethylcarbamyl chloride.

Both processes have substantial disadvantages.

Thus, in the first process, for example, a large excess of alkali metal cyanide is necessary (Org. Synth. Coll. Vol. V, 269), which renders working up more difficult and dangerous. The yields in this process are unsatisfactory in many cases, since several isomers, in particular also 4-cyanopyridines, can arise and fractionation is complicated.

A second process has the disadvantage of requiring the stoichiometric use of the expensive and highly poisonous trimethylsilyl cyanide as well as the carcinogenic N,N-dimethylcarbamyl chloride (J. Org. Chem. 48, 1375 [1983]). Because of their properties and the resultant hazard potential, both reagents are unsuitable for preparing relatively large quantities of the 2-cyanopyridines.

It has now been found, surprisingly, that substituted 1-alkoxypyridinium salts react excellently with cyanides in a polar, aprotic solvent, such as, for example, dimethylformamide, dimethylacetamide, N-methylpyrrolidone, N,N'-dimethylpropyleneurea, HMPT, acetone, acetonitrile, propionitrile, diethylene glycol dimethyl ether (diglyme), tetraglyme, tetrahydrofuran, dimethyl sulfoxide, or sulfolane, or a mixture of two or more components, to form 2-cyanopyridines, it being possible for the starting compounds to be employed in virtually equimolar ratios.

The invention relates preferably to a process for preparing compounds of the formula I

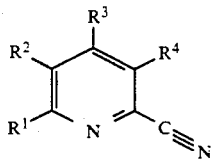

in which
- $R^1$ is H, alkyl, alkenyl, alkynyl, haloalkyl, alkoxycarbonyl, alkoxyalkyl, phenyl, benzyl or phenoxyalkyl, it being possible for the three latter radicals to be substituted in the phenyl moiety;
- $R^2$ is H, alkyl, alkenyl, alkynyl, haloalkyl or alkoxycarbonyl;
- $R^3$ is H, alkyl, alkenyl, alkynyl, haloalkyl, alkoxycarbonyl, phenyl, phenoxy, benzyl, it being possible for the three latter radicals to be substituted, or alkoxy; and
- $R^4$ is H, alkyl, alkenyl, alkynyl, haloalkyl or alkoxycarbonyl;

or
$R^1$ together with $R^2$ is a saturated chain, and the remaining radicals are as defined above;
or
$R^1$ together with $R^2$ is a chain of the formula —CH=CH—CH=CH—, which may be substituted, and the remaining radicals are as defined above;
or
$R^3$ together with $R^4$ is a chain of the formula —CH=CH—CH=CH—, which may be substituted, and the remaining radicals are as defined above;
wherein a substituted 1-alkoxypyridinium salt of the formula II,

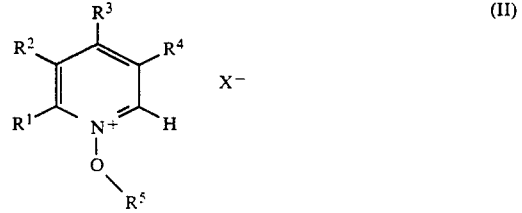

in which
$R^1$ to $R^4$ have the same meaning as in formula I and
$R^5$ is alkyl, alkenyl, alkynyl, benzyl or trialkylsilyl and
X is a leaving group;
is reacted together with a cyanide of the formula III

in which
M is alkali metal, alkaline earth metal or copper and m is 1 or 2,
in a polar, aprotic solvent or mixture of solvents.

The invention relates in particular to a process for preparing substituted 2-cyanopyridines of the formula I, in which
- $R^1$ is H, $C_1$–$C_6$-alkyl, preferably $C_1$–$C_4$-alkyl, $C_2$–$C_6$-alkenyl, $C_2$–$C_6$-alkynyl, $C_1$–$C_4$-haloalkyl, $C_1$–$C_6$-alkoxycarbonyl, $C_1$–$C_4$-alkoxy-$C_1$–$C_4$-alkyl, phenyl, benzyl or phenoxy-$C_1$–$C_2$-alkyl, it being possible for the three latter radicals to be substituted in the phenyl moiety up to five times, preferably up to three times, by identical or different radicals selected from the group comprising $C_1$–$C_4$-alkyl, preferably $C_1$–$C_2$-alkyl, halogen, $C_1$–$C_4$-alkoxy, preferably $C_1$–$C_2$-alkoxy, $C_1$–$C_4$-haloalkyl and $C_1$–$C_2$-holoalkoxy;
- $R^2$ is H, $C_1$–$C_6$-alkyl, preferably $C_1$–$C_4$-alkyl, $C_2$–$C_6$-alkenyl, $C_2$–$C_6$-alkynyl, $C_1$–$C_4$-haloalkyl or $C_1$–$C_6$-alkoxycarbonyl;
- $R^3$ is H, $C_1$–$C_6$-alkyl, preferably $C_1$–$C_4$-alkyl, $C_2$–$C_6$-alkenyl, $C_2$–$C_6$-alkynyl, $C_1$–$C_4$-haloalkyl, $C_1$–$C_6$-alkoxy-carbonyl, phenyl, phenoxy, benzyl, it being possible for the three latter radicals to be substituted up to three times by identical or different radicals selected from the group comprising $C_1$–$C_4$-alkyl, preferably $C_1$–$C_2$-alkyl, halogen, $C_1$–$C_4$-alkoxy, preferably $C_1$–$C_2$-alkoxy, $C_1$–$C_4$-haloalkyl and $C_1$–$C_2$-haloalkoxy, or $C_1$–$C_4$-alkoxy; and $R^4$ is H, $C_1$-$C_6$-alkyl, preferably $C_1$-$C_4$-alkyl, $C_2$-$C_6$-alkenyl, $C_2$-$C_6$-alkoxycarbonyl;

or $R^1$ together with $R^2$ is —(CH—)$_n$, where n is 2 to 14, preferably 3 to 12, and the remaining radicals are as defined above;

or $R^1$ together with $R^2$ is a chain of the formula —CH=CH—CH=CH—, which may be substituted by up to two identical or different radicals selected from the group comprising $C_1$-$C_4$-alkyl, preferably $CH_3$, halogen, phenoxy and $C_1$-$C_4$-alkoxy, preferably $C_1$-$C_2$-alkoxy, and the remaining radicals are as defined above;

or $R^3$ together with $R^2$ is a chain of the formula —CH=CH—CH=CH—, which may be substituted by up to two identical or different radicals selected from the group comprising $C_1$-$C_4$-alkyl, preferably $CH_3$, halogen and $C_1$-$C_4$-alkoxy, preferably $C_1$-$C_2$-alkoxy, and the remaining radicals are as defined above;

or wherein a substituted 1-alkoxypyridinium salt of the formula II, in which $R^1$ to $R^4$ have the same meaning as in formula I and
$R^5$ is $C_1$-$C_6$-alkyl, $C_2$-$C_4$-alkenyl, $C_2$-$C_4$-alkynyl, benzyl or tri-$C_1$-$C_6$-alkylsilyl and
X is a leaving group, such as halogen, $C_1$-$C_6$-alkylsulfonyloxy, $C_6$-$C_{12}$-arylsulfonyloxy, preferably phenylsulfonyloxy, wherein the latter radical may be substituted up to two times in the aryl moiety by identical or different radicals halogen or $C_1$-$C_2$-alkyl, preferably $CH_3$, $C_1$-$C_4$-haloalkylsulfonyloxy, preferably $CF_3SO_3$, or $C_1$-$C_4$-alkoxysulfonyloxy, preferably $C_1$-$C_2$-alkyloxysulfonyloxy;

is reacted together with a cyanide of the formula III, in which

M is alkali metal, alkaline earth metal or copper, preferably Na or K, and
m is 1 or 2, in a polar, aprotic solvent or mixture of solvents.

Here and hereinafter, halogen signifies fluorine, chlorine, bromine or iodine; alkyl, alkenyl and alkynyl may be straight-chain or branched, and the same is true for the alkyl moieties of the substituted radicals; the multiple bonds in alkenyl and alkynyl may be terminal or central, they may be isolated or conjugated; alkali metal signifies here and hereinafter Li, Na, K, Rb, Cs; alkaline earth metal signifies here and hereinafter Mg, Ca, Sr or Ba; the prefix "halo" signifies, here and hereinafter, that the corresponding radical is substituted wholly or partly by halogen. $CF_3$, $CHF_2$, $C_4F_9$ and $CCl_3$ may be named as examples, which are not, however, limiting.

The process according to the invention eliminates the disadvantages of the abovementioned processes that are known from the literature and thus represents a substantial technical and economic advance. It makes it possible to prepare the full range of compounds of the formula I starting from readily available compounds of the formula II (Org. Synth. Coll. Vol. V, 269) in considerably improved yields and with more favorable regioselectivity and substantially improved safety in handling.

The process according to the invention is carried out in a temperature range from −78° C. up to the boiling point of the solvent, preferably in a temperature range from −50° to 70° C., in particular in a temperature range from −30° to 30° C., in such a way that dry, finely powdered cyanide of the formula III is added to a portion of the desired solvent at the reaction temperature and the mixture is stirred vigorously. A compound of the formula II is dissolved in the remainder of the solvent. This solution is added dropwise in such a way that the temperature remains constant. Once this addition has taken place, the mixture is stirred at the desired temperature until the point in time at which the reaction is complete. This point in time can be determined by conventional methods, e.g. by thin-layer chromatographic (TLC) investigation of the reaction mixture.

In order to achieve complete reaction of the component of the formula II, it is advisable to use a small excess of the component of the formula III. The excess of this component is 1 to 20 mol %, preferably 2 to 10 mol %, in particular 2 to 5 mol %.

After the reaction has been completed, the mixture is allowed to come to room temperature and a portion of the solvent is removed by distillation, optionally under reduced pressure. The residue is distilled or added to water and extracted with a suitable solvent. After removal of the solvent, the end product of the formula I is obtained as a rule in yields of more than 90%. It can be purified by conventional purification methods, such as, for example, distillation, recrystallization or chromatography.

To avoid side reactions due to atmospheric oxygen or moisture, the process according to the invention is preferably carried out under an atmosphere of an inert gas. Examples of suitable inert gases are nitrogen or argon.

The following examples are intended to illustrate the invention, without thereby limiting it.

EXAMPLE 1

2-Cyano-6-methylpyridine (Table example no. 01)

516 g (10.5 mol) of dry, pulverized sodium cyanide were added to 3 l of dimethylformamide in a 10 l flask. A solution of 2350 g (10.3 mol) of 1-methoxy-2-methylpyridinium methyl sulfate in 1.5 l of dimethylformamide was added dropwise to this mixture at 25° C. while stirring vigorously. When the addition was complete, the mixture was stirred at room temperature for 24 hours and the insoluble components were subsequently removed by filtering with suction. The filtrate was concentrated in vacuo and the crude product was distilled through a short column. The distillate solidified to white needles (m.p.: 72–73° C.); yield: 1150 g (94.6% of Th.). b.p.: 115–117° C./0.1 mbar)

EXAMPLE 2

2-Cyano-5,6-cyclohexenopyridine (Table example no. 51)

51.5 g (1.05 mol) of sodium cyanide, which had previously been dried by standing for 12 hours in vacuo at 80° C., were suspended in 300 ml of dry dimethylformamide under argon. The mixture was cooled to −20° C., and a solution of 275.3 g (1.00 mol) of 5,6-cyclohexeno-N-methoxypyridinium methyl sulfate in 300 ml of dimethylformamide was added dropwise under argon in such a manner that the temperature remained constant. When the addition was complete, stirring was continued until the reaction was complete, and the mixture was then allowed to reach room temperature. The solvent was completely removed under reduced pressure and the residue poured into water. The mixture was extracted repeatedly with ethyl acetate, and the organic solutions were dried using sodium sulfate. After removal of the ethyl acetate, 153.5 g (97%) of brown crystals were obtained. These were recrystallized from a mixture of 1000 ml of methanol and 500 ml of water.

148.7 g (0.94 mol, 94% of theory) of 2-cyano-5,6-cyclohexenopyridine were obtained as white crystals of m.p.: 72–74° C.

$^1$H-NMR (CDCl$_3$):δ=7.55–7.31 (AB system, 2H); 3.07–2.72 (multiplet, 4H); 2.06–1.71 (multiplet, 4H)

The compounds in table 1 below can be prepared in analogy with these instructions:

| Ex. No. | R$^1$ | R$^2$ | R$^3$ | R$^4$ | m p. [°C.] |
|---|---|---|---|---|---|
| 01 | CH$_3$ | H | H | H | 72–73 |
| 02 | H | H | CH$_3$ | H | |
| 03 | CH$_3$ | CH$_3$ | H | H | Oil |
| 04 | CH$_3$ | H | CH$_3$ | H | Oil |
| 05 | CH$_3$ | CH$_3$ | CH$_3$ | H | |
| 06 | CH$_3$ | CH$_3$ | CH$_3$ | CH$_3$ | |
| 07 | C$_6$H$_5$—CH$_2$ | H | H | H | 84–86 |
| 08 | CH$_6$H$_5$—CH$_2$ | CH$_3$ | H | H | |
| 09 | C$_6$H$_5$—CH$_2$ | CH$_3$ | CH$_3$ | H | |
| 10 | C$_6$H$_5$—CH$_2$ | H | CH$_3$ | CH$_3$ | |
| 11 | C$_6$H$_5$—CH$_2$ | C$_6$H$_5$—CH$_2$ | H | H | |
| 12 | 4-F—C$_6$H$_4$CH$_2$ | H | H | H | |
| 13 | 4-Cl—C$_6$H$_4$—CH$_2$ | H | H | H | 97–99 |
| 14 | 4-Br—C$_6$H$_4$—CH$_2$ | H | H | H | |
| 15 | 4-CH$_3$—C$_6$H$_4$—CH$_2$ | H | H | H | |
| 16 | 4-CH$_3$O—C$_6$H$_4$—CH$_2$ | H | H | H | |
| 17 | 2-F—C$_6$H$_4$—CH$_2$ | H | H | H | |
| 18 | 2-Cl—C$_6$H$_4$—CH$_2$ | H | H | H | |
| 19 | 2,4-F$_2$—C$_6$H$_3$—CH$_2$ | H | H | H | |
| 20 | 2,4-Cl$_2$—C$_6$H$_3$—CH$_2$ | H | H | H | |
| 21 | 2-F-4-CH$_3$—C$_6$H$_3$—CH$_2$ | H | H | H | |
| 22 | C$_2$H$_5$ | H | H | H | |
| 23 | C$_2$H$_5$ | C$_2$H$_5$ | H | H | |
| 24 | C$_2$H$_5$ | H | C$_2$H$_5$ | H | |
| 25 | C$_2$H$_5$ | C$_2$H$_5$ | C$_2$H$_5$ | H | |
| 26 | n-C$_4$H$_9$ | H | H | H | |
| 27 | n-C$_6$H$_{13}$ | H | H | H | |
| 28 | C$_6$H$_5$ | H | H | H | |
| 29 | CH$_3$ | H | C$_6$H$_5$ | H | |
| 30 | H | H | C$_6$H$_5$—CH$_2$ | H | |
| 31 | H | H | 4-F—C$_6$H$_4$—CH$_2$ | H | |
| 32 | H | H | 4-Cl—C$_6$H$_4$—CH$_2$ | H | |
| 33 | H | H | 4-CH$_3$—C$_6$H$_4$—CH$_2$ | H | |
| 34 | H | H | 4-CH$_3$O—C$_6$H$_4$—CH$_2$ | H | |
| 35 | CH$_3$ | H | C$_6$H$_5$—CH$_2$ | H | |
| 36 | CH$_3$ | CH$_3$ | C$_6$H$_5$—CH$_2$ | H | |
| 37 | H | H | C$_6$H$_5$ | H | 65–66 |
| 38 | H | H | C$_2$H$_5$ | H | 83–85 |
| 39 | C$_3$H$_7$ | H | H | H | Oil |
| 40 | C$_3$H$_7$ | H | CH$_3$ | H | Oil |
| 41 | 4-Cl—C$_6$H$_4$—CH$_2$OCH$_2$ | H | H | H | |
| 42 | CH$_3$—OCH$_2$ | H | H | H | |
| 43 | 4-Cl—C$_6$H$_4$ | H | H | H | |
| 44 | CH$_3$—OCH$_2$ | H | CH$_3$ | H | |
| 45 | CF$_3$CF$_2$ | H | H | H | |
| 46 | 4-F—C$_6$H$_4$—CH$_2$OCH$_2$ | H | H | H | |
| 47 | 4-Cl—C$_6$H$_4$—CH$_2$OCH$_2$ | CH$_3$ | H | H | |
| 48 | 4-F—C$_6$H$_4$—CH$_2$OCH$_2$ | CH$_3$ | H | H | |
| 49 | 4-F—C$_6$H$_4$ | CH$_3$ | CH$_3$ | H | |
| 50 | —CH$_2$—CH$_2$—CH$_2$— | | H | H | 97–98 |
| 51 | —CH$_2$—CH$_2$—CH$_2$—CH$_2$— | | H | H | 72–74 |
| 52 | —CH$_2$—CH$_2$—CH$_2$—CH$_2$—CH$_2$—CH$_2$— | | H | H | 85–86 |
| 53 | —CH$_2$—CH$_2$—CH$_2$—CH$_2$—CH$_2$—CH$_2$— | | H | H | |
| 54 | —CH$_2$—(CH$_2$—)$_6$CH$_2$— | | H | H | |
| 55 | —CH$_2$—(CH$_2$—)$_8$CH$_2$— | | H | H | 79–80 |
| 56 | —CH$_2$—(CH$_2$—)$_{10}$CH$_2$— | | H | H | |
| 57 | —CH$_2$—CH$_2$—CH$_2$—CH$_2$ | | CH$_3$ | H | |
| 58 | —CH$_2$—CH$_2$—CH$_2$—CH$_2$—CH$_2$— | | C$_6$H$_5$ | H | |
| 59 | —CH$_2$—CH$_2$—CH$_2$—CH$_2$—CH$_2$ | | C$_6$H$_5$—CH$_2$ | H | |
| 60 | —CH$_2$—CH$_2$—CH$_2$—CH$_2$— | | CH$_3$ | CH$_3$ | |
| 61 | —CH$_2$—CH$_2$—CH$_2$—CH$_2$—CH$_2$— | | C$_2$H$_5$ | C$_2$H$_5$ | |
| 62 | —CH$_2$—CH$_2$—CH$_2$—CH$_2$ | | 4-F—C$_6$H$_4$—CH$_2$ | H | |
| 63 | —CH=CH—CH=CH— | | H | H | |
| 64 | —CH=CH—CH=CH— | | CH$_3$ | H | 79–81 |
| 65 | —CH=CH—CH=CH— | | OCH$_3$ | H | |
| 66 | —CH=CH—C(OCH$_3$)=CH— | | H | H | 177 |
| 67 | —C(CH$_3$)=CH—CH=CH— | | H | H | 127 |
| 68 | —CH=CH—CH=CH— | | C$_6$H$_5$ | H | |
| 69 | —CH=CH—CH=CH— | | CH$_3$ | CH$_3$ | |
| 70 | H | H | —CH=CH—CH=CH— | | 85 |
| 71 | CH$_3$ | H | —CH=CH—CH=CH— | | |

-continued

| Ex. No. | R[1] | R[2] | R[3] | R[4] | m p. [°C.] |
|---|---|---|---|---|---|
| 72 | Cl | H | —CH=CH—CH=CH— | | |
| 73 | H | Cl | —CH=CH—CH=CH— | | |
| 74 | OCH$_3$ | H | —CH=CH—CH=CH— | | |
| 75 | H | OCH$_3$ | —CH=CH—CH=CH— | | |
| 76 | —CH$_2$—CH$_2$—CH$_2$—CH$_2$— | | H | CH$_3$ | 79–80 |
| 77 | —C(OCH$_3$)=CH—CH=CH— | | H | H | 105–106 |
| 78 | CH$_3$—CH=CH—CH$_2$—CH$_2$ | H | H | H | |
| 79 | HC≡C—(CH$_2$—)$_4$ | H | H | H | |
| 80 | CH$_3$—(CH$_2$—)$_3$—C≡C | H | H | H | |

$^1$H-NMR (CDCl$_3$): [δ in ppm]
s = singlet; d = doublet; t = triplet; q = quartet. m = multiplet Cmpd. no.:
3δ=7.56(d,1H); 7.48(d,1H); 2.98(s,3H); 2.87(s,3H)
4δ=7.32(s,1H); 7.18(s,1H); 2.58(s,3H); 2.39(s,3H)
22δ=7.79(t,1H); 7.51(d,1H); 7.41(d,1H); 2,87(q,2H); 1.31(t,3H)
39δ=7.79(d,1H); 7.48(d,1H); 7.40(d,1H); 2.84(t,2H); 1.80(m,2H); 0.97(t,3H)

We claim:

1. A process for preparing substituted 2-cyanopyridines by reacting the corresponding 1-alkoxypyridinium salts with metal cyanides, wherein these compounds are reacted with each other in a polar, aprotic solvent or a mixture of such solvents.

2. The process as claimed in claim 1 for preparing compounds of the formula I,

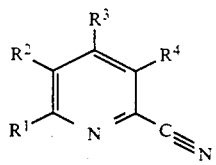
(I)

in which
R[1] is H, alkyl, alkenyl, alkynyl, haloalkyl, alkoxycarbonyl, alkoxyalkyl, phenyl, benzyl or phenoxyalkyl, it being possible for the three latter radicals to be substituted in the phenyl moiety;
R[2] is H, alkyl, alkenyl, alkynyl, haloalkyl or alkoxycarbonyl;
R[3] is H, alkyl, alkenyl, alkynyl, haloalkyl, alkoxycarbonyl, phenyl, phenoxy, benzyl, it being possible for the three latter radicals to be substituted, or alkoxy; and
R[4] is H, alkyl, alkenyl, alkynyl, haloalkyl or alkoxycarbonyl;
or
R[1] together with R[2] is a saturated chain, and the remaining radicals are as defined above;
or
R[1] together with R[2] is a chain of the formula —CH=CH—CH=CH—, which may be substituted, and the remaining radicals are as defined above;
or
R[3] together with R[4] is a chain of the formula —CH=CH—CH=CH—, which may be substituted, and the remaining radicals are as defined above;
wherein a substituted 1-alkoxypyridinium salt of the formula II,

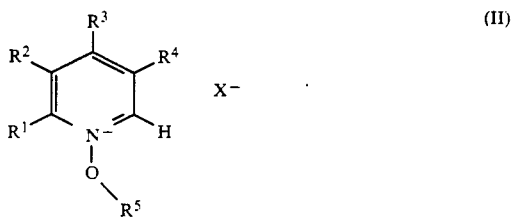

in which
R[1] to R[4] have the same meaning as in formula I and
R[5] is alkyl, alkenyl, alkynyl, benzyl or trialkylsilyl and X is a leaving group;
is reacted together with a cyanide of the formula III M(CN)$_m$ (III).

in which
M is alkali metal, alkaline earth metal or copper and m is 1 or 2, in a polar, aprotic solvent or mixture of solvents.

3. The process as claimed in claim 1, for preparing compounds of the formula I in which
R[1] is H, C$_1$-C$_6$-alkyl, C$_2$-C$_6$-alkenyl, C$_2$-C$_6$-alkynyl, C$_1$-C$_4$-haloalkyl, C$_1$-C$_6$-alkoxycarbonyl, C$_1$-C$_4$-alkoxy-C$_1$-C$_4$-alkyl, phenyl, benzyl or phenoxy-C$_1$-C$_2$-alkyl, it being possible for the three latter radical to be substituted in the phenyl moiety up to five times by identical or different radicals selected from the group comprising C$_1$-C$_4$-alkyl, halogen, C$_1$-C$_4$-alkoxy, C$_1$-C$_4$-haloalkyl and C$_1$-C$_2$-haloalkoxy;
R[2] is H, C$_1$-C$_6$-alkyl, C$_2$-C$_6$-alkenyl, C$_2$-C$_6$-alkynyl, C$_1$-C$_4$-haloalkyl or C$_1$-C$_6$-alkoxycarbonyl;
R[3] is H, C$_1$-C$_6$-alkyl, C$_2$-C$_6$-alkenyl, C$_2$-C$_6$-alkrl, C$_1$-C$_4$-haloalkyl, C$_1$-C$_6$-alkoxycarbonyl, phenyl, phenoxy, benzyl, it being possible for the three latter radicals to be substituted up to three times by identical or different radicals selected from the group comprising C$_1$-C$_4$-alkyl, halogen, C$_1$-C$_4$-alkoxy, C$_1$-C$_4$-haloalkyl and C$_1$-C$_2$-haloalkoxy, or C$_1$-C$_4$-alkoxy; and
R[4] is H, C$_1$-C$_6$-alkyl, C$_2$-C$_6$-alkenyl, C$_2$-C$_6$-alkynyl, C$_1$-C$_4$-haloalkyl or C$_1$-C$_6$-alkoxycarbonyl;
or
R[1] together with R[2] is —(CH$_2$—)$_n$, where n is 2 to 14, and the remaining radicals are as defined above;
or
R[1] together with R[2] is a chain of the formula —CH=CH—CH=CH—, which may be substituted by up to two identical or different radicals selected from the group comprising C$_1$-C$_4$-alkyl, halogen, phenoxy and $C_1$–$C_4$-alkoxy, and the remaining radicals are as defined above;
or $R^3$ together with $R^4$ is a chain of the formula —CH=CH—CH=CH— which may be substituted by up to two identical or different radicals selected from the group comprising $C_1$–$C_4$-alkyl, halogen and $C_1$–$C_4$-alkoxy, and the remaining radicals are as defined above;

wherein a substituted 1-alkoxypyridinium salt of the formula II, in which
$R^1$ to $R^4$ have the same meaning as in formula I and
$R^1$ is $C_1$–$C_6$-alkyl, $C_2$–$C_4$-alkenyl, $C_2$–$C_4$-alkynyl, benzyl or tri-$C_1$–$C_6$-alkylsilyl and
X is a leaving group:
is reacted with a cyanide of the formula III, in which
M is alkali metal, alkaline earth metal or copper and m is 1 or 2.

4. The process as claimed in claim 1, wherein the leaving group X is a radical selected from the group comprising halogen, $C_1$–$C_6$-alkylsulfonyloxy, $C_6$–$C_{12}$-arylsulfonyloxy, it being possible for the latter radical to be substituted up to two times in the aryl moiety by identical or different radicals halogen or $C_1$–$C_2$-alkyl, $C_1$–$C_4$-haloalkylsulfonyloxy or $C_1$–$C_4$-alkoxysulfonyloxy.

5. The process as claimed in claim 1, wherein the reaction is carried out in dimethylformamide or in a mixture of solvents containing the latter.

6. The process as claimed in claim 1, wherein the metal cyanide is employed in an excess of 1 to 20 mol % relative to the 1-alkoxypyridinium salt.

7. The process as claimed in claim 6, wherein the metal cyanide is employed in an excess of 2 to 10 mol % relative to the 1-alkoxypyridinium salt.

8. The process as claimed in claim 7, wherein the metal cyanide is employed in an excess of 2 to 5 mol % relative to the 1-alkoxypyridinium salt.

9. The process as claimed in claim 1, wherein the temperature range for the reaction of compounds of the formulae II and III is between −50° C. and +70° C.

10. The process as claimed in claim 9, wherein the temperature range for the reaction of compounds of the formulae II and III is between −30° C. and +30° C.

* * * * *